(12) United States Patent
Schuessler

(10) Patent No.: US 9,387,068 B2
(45) Date of Patent: *Jul. 12, 2016

(54) SELF-SEALING SHELL FOR INFLATABLE PROSTHESES

(71) Applicant: Allergan, Inc., Irvine, CA (US)

(72) Inventor: David Schuessler, Ventura, CA (US)

(73) Assignee: Allergan, Inc., Irvine (*) Notice: Subject to any disclaimer, the term of this patent is extended or adjusted under 35 U.S.C. 154(b) by 484 days.

This patent is subject to a terminal disclaimer.

(21) Appl. No.: 13/741,093

(22) Filed: Jan. 14, 2013

(65) Prior Publication Data

US 2013/0131799 A1   May 23, 2013

Related U.S. Application Data

(62) Division of application No. 12/543,795, filed on Aug. 19, 2009, now Pat. No. 8,690,943.

(60) Provisional application No. 61/090,328, filed on Aug. 20, 2008.

(51) Int. Cl.
  *A61F 2/12* (2006.01)
  *A61B 19/00* (2006.01)
  *A61F 5/00* (2006.01)

(52) U.S. Cl.
  CPC . *A61F 2/12* (2013.01); *A61B 19/24* (2013.01); *A61F 5/003* (2013.01); *A61F 5/0036* (2013.01); *A61F 2210/0061* (2013.01); *A61F 2250/0003* (2013.01)

(58) Field of Classification Search
  CPC .................................. A61F 2/12; A61B 19/14
  USPC ........................................................ 623/7–8
  See application file for complete search history.

(56) References Cited

U.S. PATENT DOCUMENTS

| | | |
|---|---|---|
| 3,204,959 A | 9/1965 | Nichols |
| 3,301,251 A | 1/1967 | Jackson |
| 3,301,254 A | 1/1967 | Schickedanz |
| 3,577,836 A | 5/1971 | Tamura |
| 3,852,832 A | 12/1974 | McGhan et al. |
| 3,919,724 A | 11/1975 | Sanders et al. |
| 4,157,085 A | 6/1979 | Austad |
| 4,190,040 A | 2/1980 | Schulte |
| 4,200,098 A * | 4/1980 | Ayer et al. ............. 424/424 |
| 4,332,634 A | 6/1982 | Aperavich |
| 4,428,364 A | 1/1984 | Bartolo |
| 4,455,691 A | 6/1984 | Van Aken Redinger et al. |
| 4,605,412 A | 8/1986 | LaForest et al. |
| 4,636,213 A | 1/1987 | Pakiam |
| 4,650,487 A | 3/1987 | Chaglassian |
| 4,662,357 A | 5/1987 | Pierce et al. |
| 4,685,447 A | 8/1987 | Iversen et al. |

(Continued)

FOREIGN PATENT DOCUMENTS

| | | |
|---|---|---|
| EP | 0029292 B1 | 5/1981 |
| EP | 0324234 | 7/1989 |

(Continued)

*Primary Examiner* — Suzette J Gherbi
(74) *Attorney, Agent, or Firm* — Linda Allyson Nassif

(57) ABSTRACT

A self-sealing shell useful as a component of a soft fluid-filled prosthetic implant is provided. The shell is at least partly constructed of a wall made of a colloid of an elastomeric polymer matrix and particles of a water-swellable material distributed therein.

6 Claims, 2 Drawing Sheets

(56) References Cited

U.S. PATENT DOCUMENTS

| | | | |
|---|---|---|---|
| 4,738,657 A | 4/1988 | Hancock et al. | |
| 4,773,909 A | 9/1988 | Chaglassian | |
| 4,840,615 A | 6/1989 | Hancock et al. | |
| 4,889,744 A | 12/1989 | Quaid | |
| 4,908,029 A | 3/1990 | Bark et al. | |
| 4,969,906 A | 11/1990 | Kronman | |
| 5,005,591 A | 4/1991 | Austad | |
| 5,019,101 A | 5/1991 | Purkait et al. | |
| 5,022,942 A | 6/1991 | Yan et al. | |
| 5,026,394 A | 6/1991 | Baker | |
| 5,066,303 A | 11/1991 | Bark et al. | |
| 5,074,878 A | 12/1991 | Bark et al. | |
| 5,084,061 A | 1/1992 | Gau et al. | |
| 5,127,627 A | 7/1992 | Wiser | |
| 5,133,753 A | 7/1992 | Bark et al. | |
| 5,141,508 A | 8/1992 | Bark et al. | |
| 5,171,269 A | 12/1992 | Bark | |
| 5,282,857 A * | 2/1994 | Perry et al. | 623/8 |
| 5,340,352 A | 8/1994 | Nakanishi et al. | |
| 5,425,762 A | 6/1995 | Muller | |
| 5,447,535 A | 9/1995 | Muller | |
| 5,456,716 A | 10/1995 | Iversen et al. | |
| 5,480,430 A | 1/1996 | Carlisle et al. | |
| 5,496,368 A * | 3/1996 | Wiese | 623/8 |
| 5,525,275 A | 6/1996 | Iversen et al. | |
| 5,536,264 A * | 7/1996 | Hsueh et al. | 604/368 |
| 5,571,183 A | 11/1996 | Kazem et al. | |
| 5,589,176 A | 12/1996 | Seare, Jr. | |
| 5,632,774 A | 5/1997 | Babiam | |
| 5,674,285 A | 10/1997 | Quaid | |
| 5,895,423 A | 4/1999 | Becker et al. | |
| 5,964,803 A | 10/1999 | Iversen et al. | |
| 6,022,376 A | 2/2000 | Assell et al. | |
| 6,074,421 A | 6/2000 | Murphy | |
| 6,214,045 B1 | 4/2001 | Corbitt, Jr. et al. | |
| 6,214,331 B1 | 4/2001 | Vanderhoff et al. | |
| 6,228,116 B1 | 5/2001 | Ledergerber | |
| 6,231,712 B1 * | 5/2001 | Torres | 156/204 |
| 6,232,372 B1 * | 5/2001 | Brothers et al. | 523/206 |
| 6,602,452 B2 | 8/2003 | Schuessler | |
| 6,692,527 B1 | 2/2004 | Bellin et al. | |
| 6,692,528 B2 * | 2/2004 | Ward et al. | 623/17.12 |
| 6,733,512 B2 | 5/2004 | McGhan | |
| 6,743,254 B2 | 6/2004 | Guest et al. | |
| 6,913,765 B2 * | 7/2005 | Li et al. | 424/426 |
| 6,955,690 B1 | 10/2005 | Cao | |
| 6,962,739 B1 | 11/2005 | Kim et al. | |
| 7,018,692 B2 | 3/2006 | Kim et al. | |
| 7,914,578 B2 * | 3/2011 | Vardi | 623/8 |
| 7,976,859 B2 | 7/2011 | Beisang et al. | |
| 8,066,758 B2 * | 11/2011 | Bogert et al. | 623/1.13 |
| 8,070,809 B2 | 12/2011 | Schuessler | |
| 8,377,127 B2 | 2/2013 | Schuessler et al. | |
| 8,609,004 B2 | 12/2013 | Schuessler | |
| 8,670,633 B2 | 3/2014 | Boyden et al. | |
| 8,690,943 B2 * | 4/2014 | Schuessler | 623/8 |
| 8,968,400 B2 * | 3/2015 | Schuessler | 623/8 |
| 2001/0052141 A1 | 12/2001 | Andersen | |
| 2002/0106953 A1 | 8/2002 | Kim et al. | |
| 2003/0134067 A1 | 7/2003 | Garelli | |
| 2003/0149481 A1 | 8/2003 | Guest et al. | |
| 2003/0171768 A1 | 9/2003 | McGhan | |
| 2003/0205846 A1 | 11/2003 | Bellin et al. | |
| 2003/0233150 A1 * | 12/2003 | Bourne et al. | 623/23.72 |
| 2005/0170221 A1 | 8/2005 | Kim et al. | |
| 2007/0059375 A1 | 3/2007 | Bourne et al. | |
| 2007/0196454 A1 | 8/2007 | Stockman et al. | |
| 2007/0198085 A1 | 8/2007 | Benslimane | |
| 2008/0027534 A1 | 1/2008 | Edwin et al. | |
| 2008/0063716 A1 * | 3/2008 | Moro et al. | 424/484 |
| 2008/0312739 A1 | 12/2008 | Agerup et al. | |
| 2009/0012372 A1 | 1/2009 | Burnett et al. | |
| 2009/0030515 A1 | 1/2009 | Schuessler et al. | |
| 2009/0048684 A1 * | 2/2009 | Lesh | 623/23.72 |
| 2009/0118756 A1 | 5/2009 | Valencon et al. | |
| 2009/0118829 A1 | 5/2009 | Powell et al. | |
| 2009/0198332 A1 | 8/2009 | Becker | |
| 2009/0198333 A1 | 8/2009 | Becker | |
| 2009/0202608 A1 | 8/2009 | Alessi et al. | |
| 2009/0270904 A1 | 10/2009 | Birk et al. | |
| 2009/0270985 A1 | 10/2009 | Schuessler | |
| 2009/0275974 A1 | 11/2009 | Marchand et al. | |
| 2009/0326654 A1 * | 12/2009 | Powell | 623/8 |
| 2010/0049316 A1 | 2/2010 | Schuessler | |
| 2010/0070042 A1 | 3/2010 | Bryan et al. | |
| 2010/0168853 A1 | 7/2010 | Job | |
| 2011/0054407 A1 | 3/2011 | Olroyd | |
| 2011/0270391 A1 | 11/2011 | Chitre et al. | |
| 2011/0288639 A1 | 11/2011 | Trilokekar et al. | |
| 2011/0306827 A1 | 12/2011 | Chitre et al. | |
| 2012/0109080 A1 | 5/2012 | Manesis et al. | |
| 2012/0123537 A1 * | 5/2012 | Manesis et al. | 623/8 |
| 2012/0197393 A1 | 8/2012 | Yu | |
| 2012/0303120 A1 | 11/2012 | Schuessler | |
| 2013/0052142 A1 * | 2/2013 | Harder et al. | 424/9.411 |
| 2013/0131799 A1 | 5/2013 | Schuessler | |
| 2013/0131801 A1 | 5/2013 | Schuessler et al. | |
| 2013/0171288 A1 | 7/2013 | Harders | |
| 2013/0245758 A1 | 9/2013 | Chitre et al. | |
| 2013/0304207 A1 | 11/2013 | Schuessler | |
| 2013/0325120 A1 | 12/2013 | McClellan | |

FOREIGN PATENT DOCUMENTS

| | | |
|---|---|---|
| EP | 0412703 | 2/1991 |
| EP | 0422302 | 4/1991 |
| EP | 0478279 | 4/1992 |
| EP | 0784987 | 7/1997 |
| EP | 0872221 B1 | 2/1999 |
| FR | 587637 | 4/1925 |
| FR | 895747 | 2/1945 |
| GB | 2392077 | 2/2004 |
| WO | 9220519 | 11/1992 |
| WO | 9501864 | 1/1995 |
| WO | 0210667 | 2/2002 |
| WO | 03057462 | 7/2003 |
| WO | 03059617 | 7/2003 |
| WO | 2004021935 | 3/2004 |
| WO | 2008016983 | 2/2008 |
| WO | 2009061672 | 5/2009 |
| WO | 2010022130 | 2/2010 |
| WO | 2012061368 A1 | 5/2012 |

* cited by examiner

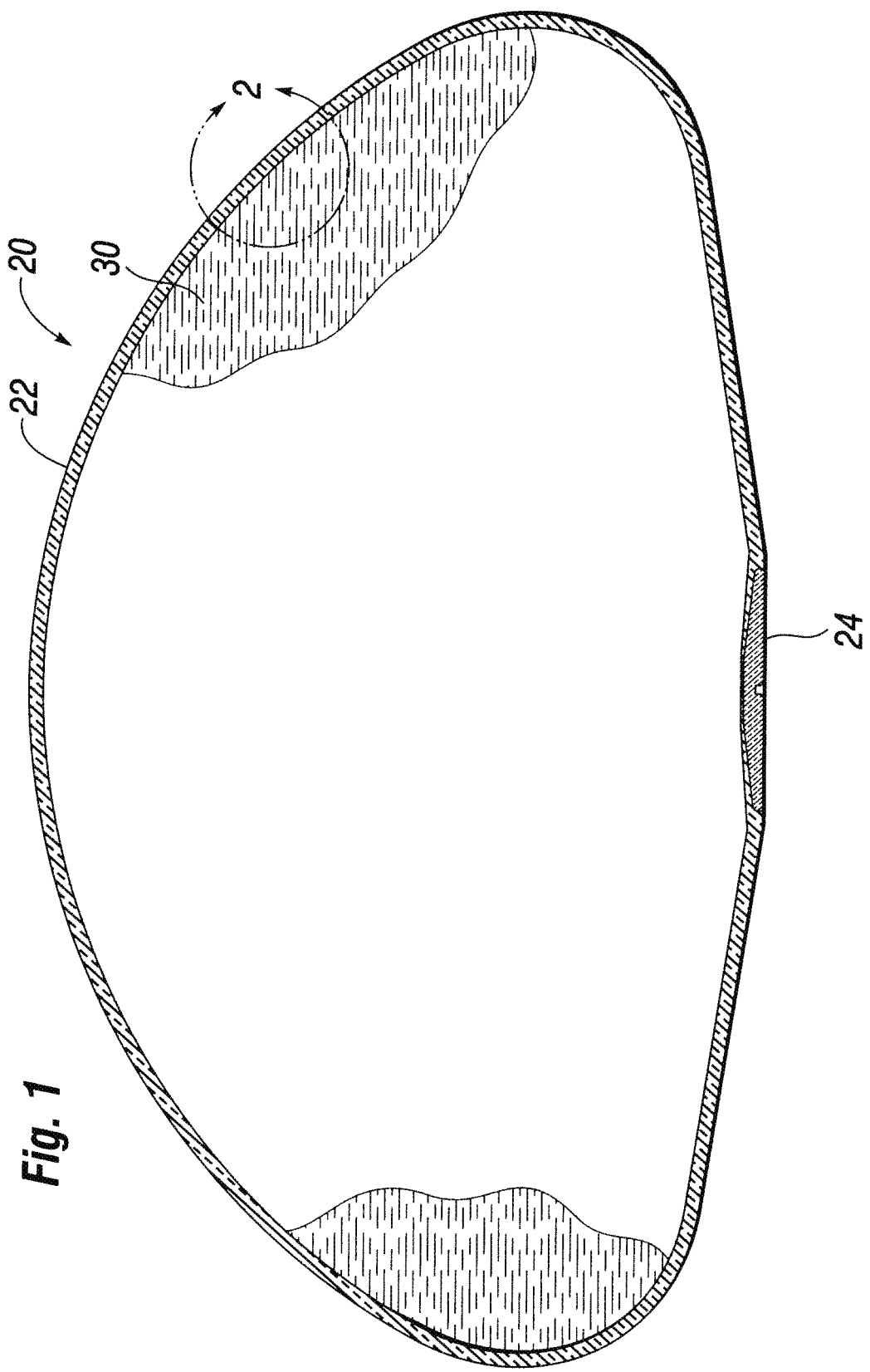

SELF-SEALING SHELL FOR INFLATABLE PROSTHESES

RELATED APPLICATION

This application is a divisional of U.S. patent application Ser. No. 12/543,795, filed Aug. 19, 2009, which claims priority to U.S. Provisional Patent Application No. 61/090,328, filed on Aug. 20, 2008, the entire disclosure of each of which is incorporated herein by this reference.

FIELD OF THE INVENTION

The present invention relates to fluid-filled prosthetic implants and, more particularly, to the construction of a self-sealing shell for an inflatable prosthesis.

BACKGROUND OF THE INVENTION

Implantable prostheses are commonly used to replace or augment body tissue. In the case of breast cancer, it is sometimes necessary to remove some or all of the mammary gland and surrounding tissue which creates a void that can be filled with a fluid-filled implantable prosthesis. The implant serves to support surrounding tissue and to maintain the appearance of the body. The restoration of the normal appearance of the body has an extremely beneficial psychological effect on post-operative patients, alleviating much of the shock and depression that often follows extensive surgical procedures.

Soft implantable prostheses typically include a relatively thin and quite flexible envelope or shell made of silicone elastomer. The shell is filled either with a silicone gel or with a physiologic saline solution. The filling of the shell may take place before or after the shell is implanted in the patient.

A saline-filled implant includes an outer shell of several layers of silicone elastomer having a valve or fill port on one side. The prosthesis is typically implanted into the breast cavity in an empty or only partially filled state. The implant is then inflated to its final size by means of the valve or fill port. This helps reduce the size of the needed incision, and enables a surgeon to adjust and even microadjust the volume of the implant. Unfortunately, the valve or fill port is sometimes noticeable to the touch.

Prior to implantation of a more permanent prosthesis, it is common practice to utilize a more temporary implant, for example, what is known as a "tissue expander" in order to gradually create the space necessary for the more permanent prosthesis. Essentially, a tissue expander comprises an inflatable body, having an inflation valve connected thereto. The valve may be formed into the inflatable body itself or may be remotely located and connected to the inflatable body by means of an elongated conduit.

The inflatable body of the tissue expander is placed subcutaneously in the patient, at the location of where tissue is to be expanded. The inflation valve, whether on the implant or remote thereto, is also subcutaneously positioned or implanted, and is configured to allow gradual introduction of fluid, typically saline, into the inflation body, by injection with a syringe. After gradual inflation at pre-determined intervals, the skin and subcutaneous tissues overlying the expander are consequently caused to expand in response to the pressure exerted upon such tissues by the inflatable body as solution is gradually introduced therein.

After gradual inflation at pre-determined intervals, which may extend over weeks or months, the skin and subcutaneous tissue will expand to the point where further medical procedures can be performed, such as the permanent implantation of a prosthesis, plastic and reconstructive surgery, or for use of the skin and subcutaneous tissue for use in some other part of the body.

During a mastectomy, a surgeon often removes skin as well as breast tissue, leaving the chest tissues flat and tight. To create a breast-shaped space for a reconstructive implant, a tissue expander is sometimes used as described above.

In any event, it should be appreciated that locating the fill valve on the prosthesis or tissue expander requires considerable practitioner skill. Attempts to make products which facilitate this include the development of various products having structure, for example, embedded magnets or a raised ring, for assisting physicians in locating the valve.

Bark, et al., U.S. Pat. No. 5,074,878, discloses a tissue expander. According to Bark et al., the tissue expander comprises a closed shell structure having a wall formed of a needle-penetrable material which has self-sealing characteristics. The shell includes a flowable self-sealing layer sandwiched between layers of non-flowable elastomeric material.

There still remains a need for better inflatable implant shells.

SUMMARY OF THE INVENTION

The present invention provides inflatable prosthetic implants, components thereof and methods of making same. Advantageously, the implants include a self-sealing shell, thus eliminating or substantially reducing the need for a traditional fill valve. It is to be appreciated that the terms "implant" "prosthesis" as used herein are intended to encompass permanent implants, as well as relatively temporary tissue expanders, and components, for example, shells, of such implantable devices.

Advantageously, the present invention is relatively simple to manufacture and straightforward in construction. Many embodiments of the present invention can be made using conventional shell manufacturing equipment and using readily commercially available materials. For example unlike many previously proposed breast implant shells allegedly having self-sealing attributes, many of the present implants do not need to be formed, molded and/or cured under a specific compression or tension.

In a broad aspect of the invention, a shell for an inflatable implant generally comprises a self-sealing layer comprising an elastomer component and particles, for example, discontinuous particles, of a swellable material dispersed in the elastomer component. In addition, the shell is structured such that when the shell is substantially dry or dehydrated, the shell is not self-sealable, and when the shell is wet or has been exposed to or contacted with an aqueous fluid, for example, water, the fluid enters the layer and causes the particles dispersed therein to swell within the elastomer component. Compressive forces resulting from the swollen particles within the elastomer component cause the shell to become self-sealing, for example, with respect to a needle puncture through the shell.

More specifically, the layer may be comprised of an elastomeric component, for example, a biocompatible, silicone-based material, and discontinuous, swellable particles dispersed throughout the elastomeric component. For example, the shell may comprise a silicone elastomer matrix having hydrogel particles distributed throughout the matrix. When contacted with an aqueous fluid, such as water or saline, the layer is penetrated by the fluid and the fluid is absorbed by the particles, causing the particles to swell or expand. Compressive forces created by the elastomeric component and the swelled particles dispersed therein cause the layer to become self-sealing, for example, self-sealing to a needle puncture when such a needle penetrates and is then withdrawn from the layer.

The self-sealing surface may be in the form of a patch used to seal a hole or aperture of a breast implant shell. In other embodiments, the self-sealing surface is larger than a conventional patch and may encompass an entire, or substantially entire, wall of the shell. Advantageously, this allows for relatively easy percutaneous fluid adjustment of the implant that does not require locating accessories or special equipment.

In some embodiments, the self-sealing material in accordance with the invention forms a shell of an inflatable gastric balloon useful for treatment of obesity.

In a more specific embodiment of the invention, the particles comprise hydrogel particles. In some embodiments, the hydrogel particles are mixed into an uncured, liquid form of the elastomeric component while the particles are in a dry or at least partially dehydrated state. The particles may comprise a polyethylene glycol, a hydroxyethylcellulose, or another suitable biocompatible hydrogel material, or mixtures thereof.

Preferably, the elastomer component comprises a silicone elastomer material that is conventionally used in the construction of flexible shells for inflatable implants. For example, the elastomer component may comprise any suitable silicone elastomeric material. Suitable silicone elastomers include, but are not limited to, homopolymers such as polydimethylsiloxane or polymethylvinylsiloxane, or copolymers such as copolymers of diphenylsiloxane and dimethylsiloxane.

The silicone elastomer can be cured by conventional means, for example, by using a polysiloxane crosslinker containing silicone-bonded hydrogen atoms with a vinyl containing siloxane elastomer and a platinum catalyst.

The present invention further provides an article of material useful as a shell for an inflatable implant, wherein the article is manufactured by the steps comprising providing hydrogel particles, for example in a substantially dry state, providing an elastomer material dispersion, mixing the hydrogel particles into the elastomer material dispersion, curing the elastomer material dispersion having the substantially dry hydrogel particles therein to obtain a useful article which has the characteristic of being self-sealable, for example, when punctured with a needle, when the article has been contacted with an aqueous fluid, for example, water or saline.

BRIEF DESCRIPTION OF THE DRAWINGS

Features and advantages of the present invention will become appreciated as the same become better understood with reference to the specification, claims, and appended drawings wherein:

FIG. 1 is a cross-sectional view through a self-sealing implant prosthesis of the present invention having a molded-in-place flush patch;

DETAILED DESCRIPTION

The present invention provides a fluid-filled inflatable prosthesis formed with a flexible outer shell having a wall that is at least partly constructed of a polymer matrix and a plurality of particles of material evenly or randomly distributed in the matrix. The shell wall self-seals around needle punctures.

The present invention is especially useful for soft fluid-filled implants, for example, but not limited to, implants useful in breast reconstruction or breast augmentation procedures.

FIG. 1 illustrates an exemplary cross-section of a prosthesis, for example, a fluid-filled breast implant 20 of the present invention. The implant 20 includes an elastomer shell 22 having an anatomical configuration, in this case, a configuration suitable for augmenting or reconstructing a human breast. The shell 22 is shown filled with a fluid such as physiologic saline 30. A patch 24 covers an aperture left over from a dipping or rotational molding process used to form the shell 22.

Figure 2A:
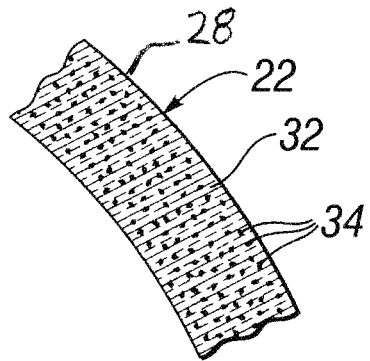
FIG. 2A is a sectional view through a portion of the wall of the self-sealing implant prosthesis of FIG. 1 prior to implant.
Figure 2B:
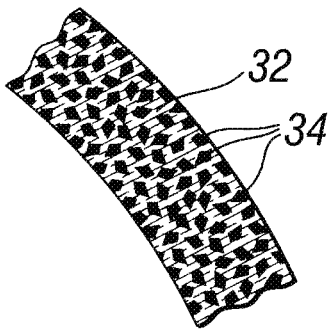
FIG. 2B is a sectional view through a portion of the wall of the self-sealing implant prosthesis of FIG. 1 after implant and absorbance of an aqueous fluid to cause swelling of particles therein.

FIG. 2A shows a wall 28 of the shell 22 prior to the shell 22 being filled with saline. The wall 28 may make up the entire shell 22 or may make up only a portion of the shell 22. The wall 28 comprises an elastomer component 32 and discontinuous particles 34 of a swellable material dispersed in the elastomer component 32. Turning now to FIG. 2B, the wall 28 is shown after having been contacted with an aqueous fluid, for example, water. When the wall 28 is contacted with an aqueous fluid, the particles 34 of swellable material enlarge such that the wall 28 becomes self-sealing to a needle puncture.

In accordance with one aspect of the invention, the wall 28 has the characteristic of being not self sealing when it is in a dry state (FIG. 2A), but nearly substantially entirely self-sealing when in the wet state (FIG. 2B), that is, after it has been contacted with water or other suitable aqueous medium. Contact with an aqueous fluid may be accomplished by exposing the shell or wall of said shell to liquid water, steam or humid environment.

The shell wall 22 includes a polymer matrix 32 and a plurality of particles 34 substantially uniformly or randomly distributed therein. It can be said that the particles 34, in a sense, are entrapped in the polymeric elastomer component 32, or occupy enclosed spaces within the elastomeric material which forms a matrix around the particles.

The polymer matrix 32 may be a silicone elastomer such as a dimethyl silicone elastomer. The polymer matrix 32 may comprise a substantially homogeneous dimethyl-diphenyl silicone elastomer. One especially advantageous composition useful in the present invention is described in Schuessler, et al., U.S. application Ser. No. 12/179,340, filed Jul. 24, 2008, albeit for gel-filled prostheses, the disclosure of which is incorporated herein in its entirety by this specific reference.

In one aspect of the present invention, the shell wall 22 comprises a colloid of the matrix 32 having the swellable particles 34 therein. A colloid in this sense generally means a material made up of a system of particles dispersed in a continuous medium. The size of the particles can vary, and they remain dispersed indefinitely in the medium. In contrast with some definitions of colloid, in accordance with the present invention the linear dimensions of the particles need not be within a specified range. For purposes of the present invention, the swellable particles may be in the form of a solid or a liquid, as long as they do not mix or otherwise dissolve into the surrounding matrix material 32.

In one embodiment, the shell wall 22 is formed by dispersing solid particles 34 in a liquid matrix 32, which is then cured. In another embodiment, the shell wall 22 is formed by creating an emulsion of liquid particles 34 immiscible in a liquid matrix 32, which is then cured. The elastomeric component of the shell wall 22 may be a non-water-swellable silicone elastomer within which water-swellable solid or liquid particles are entrapped.

In one aspect of the invention, the particles 34 are a water-swellable material which swells upon contact with an aqueous fluid. For instance, the material of the particles 34 may be a hydrogel material, or polyethylene glycol (PEG) material. The particles 34 may be in liquid or solid form, as mentioned, and the same substance may be provided in either phase.

In some embodiments, the water swellable particles 34 have a molecular weight of between about 200 and about 10,000 Daltons. In some embodiments, the particles 34 make up about 2% by weight of the particle/matrix composition. In some embodiments, the particles 34 make up at least about 2% by weight of the particle/matrix composition, up to about 40% by weight of the composition. In some embodiments, the particles make up about 25% by weight of the composition.

The combination of the polymer matrix 32 and particle 34 wall construction self-seals around needle punctures once the material has been exposed to or contacted with an aqueous fluid such as water, saline, body fluid, or other biocompatible liquid. Once contacted with an aqueous fluid, the wall 22 allows the fluid to enter the elastomer matrix and upon contacting the particles 34, the particles 34 swell and expand as shown in FIG. 2B. Although not wishing to be bound by any specific theory of operation, it is believed that the swelling of the particles 34 creates compressive forces in the wall which makes the shell self-sealing to puncture, for example, with a standard gauge needle.

Various processes are known for forming the flexible implant shells for implantable prostheses and tissue expanders of the present invention. In each, a plurality of the particles 34 of the water-swellable material are distributed in a quantity of the liquid polymer matrix 32 to form a colloid. Again, the particles 34 may be in solid or liquid form. The colloid is then solidified to form a portion of the shell wall 22. The colloid may be formed as a sheet material and used for a patch of an otherwise non-self-sealing shell, or may be used as the entire shell, including the patch. In the former case, the colloid first solidifies and is then formed into part of the shell, while in the latter case, the colloid simultaneously solidifies and forms the shell. The shell is then exposed to an aqueous fluid (such as by filling with saline) such that the particles swell and the colloidal portion of the shell wall is capable of self-sealing around needle punctures. In one process, a suitably shaped mandrel may be dipped one or more times into a dispersion of the polymer matrix with distributed water-swellable particles. Each time the mandrel is withdrawn from the dispersion and the excess is allowed to drain from the mandrel. After the excess dispersion has drained from the mandrel at least a portion of solvent within the dispersion is allowed to evaporate to stabilize the silicone elastomer coating. Also, curing may take place between dippings. The process is then repeated several times until a shell of the desired thickness is formed. Furthermore, the layered structure of current silicone elastomer shells can be made by sequentially dipping the mandrel in different dispersions.

In one embodiment, the invention comprises forming an elastomer shell 22 within an injection or rotational molding system. A liquid quantity of the polymer matrix with distributed water-swellable particles is introduced within a mold cavity, which then may be rotated about multiple axes. The liquid evenly coats the inside of the mold cavity as it rotates, and heat is applied to cure the liquid to a more solid form. One exemplary rotational molding system disclosed in U.S. Pat. No. 7,165,964 to Schuessler, the entire disclosure of which is incorporated herein, incorporates a vent system to remove volatilized solvents, and a mold liner to eliminate a mold seam. The patch 24 may be molded in place within the mold cavity, as disclosed in U.S. patent application Ser. No. 12/431,070 filed Apr. 28, 2009, and having common inventor and common assignee herewith, the entire disclosure of which is incorporated herein by this specific reference.

In one embodiment, the implant 20 is a breast implant or a tissue expander for a breast. The implant 20 may be inserted into a breast cavity in an empty or partially-filled state. Introducing an implant that is not completely filled naturally reduces the required size of the incision, which is beneficial as it leaves a smaller scar. Once in place the surgeon fills the hollow interior of the shell 22 with an appropriate fluid 30 such as physiologic saline via a needle. Advantageously, the entire shell wall, and preferably also the patch 24, is formed of the self-sealing construction and thus there is little trouble locating an appropriate injection site.

In another embodiment, the implant 20 is an inflatable member of a gastric balloon useful for treatment of obesity.

Figure 3A:
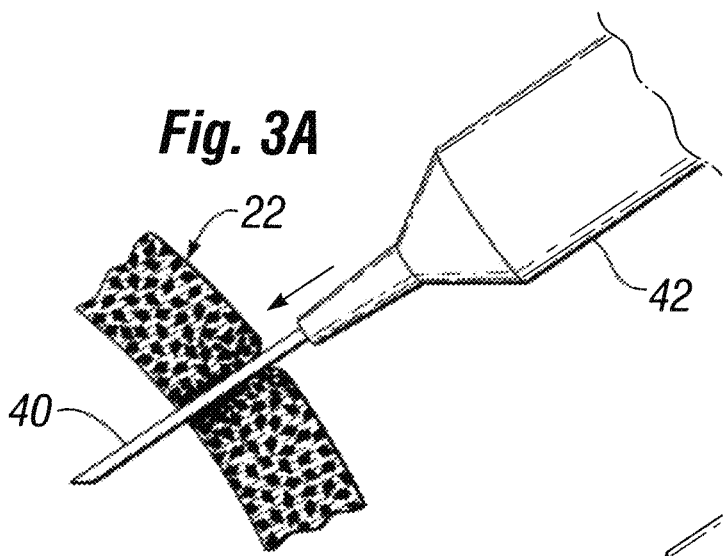
FIGS. 3A-3B show needle puncture of and subsequent withdrawal from the implant prosthesis wall of FIG. 1 illustrating a self-sealing character of the wall.

FIG. 3A illustrates a needle 40 attached to a syringe 42 penetrating a location in the shell wall 22. An additional quantity of the fluid 30 is then injected into the shell 22 to either incrementally expand the shell, as with tissue expanders, or fill the shell to a predetermined volume. The final volume varies depending on the desired outcome. Additional fluid adjustments may be desired to fine tune the final volume. In that case, a needle is again used to either remove or add fluid.

Figure 3B:
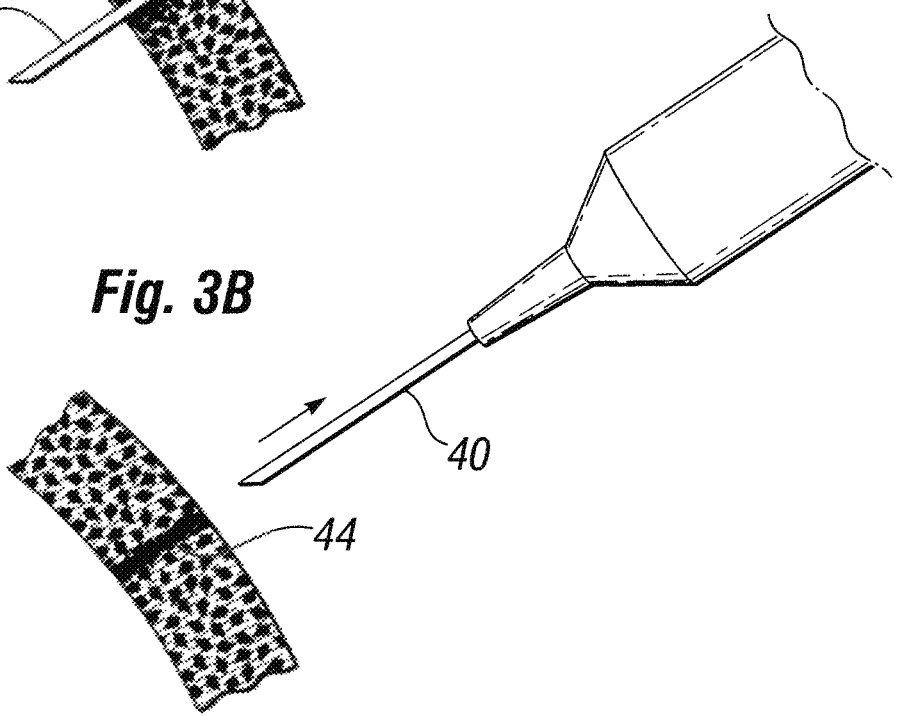

FIG. 3B shows the shell wall 22 after removal of the needle 40. The swelled particles 34 tend to migrate into the puncture created by the needle 40, and form a seal 44 in the puncture. Multiple punctures at different locations may be made in the shell 22, all of which seal as in FIG. 3B. The advantage of having the entire shell 22 available for injection will be obvious to those of skill in the art.

As mentioned above, the entire shell 22 of the inflatable prosthesis may comprise a single layer of the matrix 32 and particles 34 around the entire shell. Alternatively, however, just a portion of the shell 22, such as an anterior face, may include the self-sealing characteristic in accordance with the invention.

The present invention further provides methods of making an implantable soft prosthesis. The methods generally comprise the steps of providing a liquid polymer matrix such as a silicone elastomer in a flowable form and distributing particles of a water-swellable material in the polymer matrix to form a fluid elastomer/particle mixture, for example, a colloid. While in a fluid state, the mixture is formed into a membrane or layer which, when solidified, can be used to form at least a part of a shell wall for an inflatable prosthesis. In order to cause the prosthesis to become self-sealing as described and shown elsewhere herein, the wall is contacted with or exposed to an aqueous fluid.

In one embodiment, the region of the shell having the self-sealing colloid of the matrix 32 and particles 34 is approximately ½ or more of the surface area of the entire shell. Still further, a fill patch over a manufacturing aperture in the shell may be the only portion of the implant which is self-sealing in accordance with the invention.

EXAMPLE

A silicone elastomer dispersion (polydimethyl siloxane dispersed in a xylene solvent such as NuSil MED-6640) at approximately 1000 cps is mixed with polyethylene glycol (8000 MW) powder in a ratio of about 10% by weight of silicone solids.

This mixture is dip cast over a mandrel in the desired shape of the shell. The mixture is dipped several times to achieve a thickness of 0.050" on the mandrel surface after air drying and removal of the solvent. The shell is cured at about 121 C for about 90 minutes. The shell is removed from the mandrel. After being contacted with water, the shell is self sealing to a needle puncture.

It is contemplated that the self sealing materials of the present invention may be formed into very thin laminates which are applied in a layered fashion to traditional silicone elastomeric shells. It is further contemplated that the self-sealing material may make up one or more layers of a shell which are sandwiched between layers of silicone elastomer such that the self sealing layer is spaced apart from inner and outer surfaces of the shell wall.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. An implantable article of manufacture useful as a component of an inflatable prosthesis, the article made by the steps of:

providing a curable polymer-based liquid;

distributing a plurality of solid, water swellable particles in the liquid to form a fluid mixture comprising a liquid polymer and solid, water swellable particles;

allowing the mixture to solidify to form a polymeric matrix having solid, water swellable particles occupying enclosed spaces in the matrix; and forming the mixture into a wall of an inflatable prosthesis;

wherein, when the wall is contacted with an aqueous fluid, the water swellable particles expand and the wall becomes self-sealing to a needle puncture.

2. The article of claim 1 wherein the wall is not self sealing to a needle puncture when it is in a dry state.

3. The article of claim 1 wherein the particles comprise hydrogel particles.

4. The article of claim 1 wherein the particles comprise a hydrogel comprising polyethylene glycol.

5. The article of claim 1 wherein the water swellable particles make up between about 2% to about 40% by weight of the mixture.

6. The article of claim 1 wherein the water swellable particles make up about 25% by weight of the mixture.

* * * * *